US00PP27977P3

(12) United States Plant Patent
Kordes

(10) Patent No.: US PP27,977 P3
(45) Date of Patent: May 9, 2017

(54) GRANDIFLORA ROSE PLANT NAMED 'KORFRE0007'

(50) Latin Name: *Rosa hybrida*
Varietal Denomination: KORfre0007

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop ( * ) Notice: Subject to any disclaimer, the term of this patent is extended or adjusted under 35 U.S.C. 154(b) by 135 days.

(21) Appl. No.: 14/756,004

(22) Filed: Jul. 17, 2015

(65) Prior Publication Data

US 2016/0029525 P1 Jan. 28, 2016

Related U.S. Application Data

(60) Provisional application No. 61/999,355, filed on Jul. 23, 2014.

(51) Int. Cl.
*A01H 5/02* (2006.01)

(52) U.S. Cl.
USPC ..... Plt./132

(58) Field of Classification Search
USPC ..... Plt./101, 130, 132, 137
See application file for complete search history.

*Primary Examiner* — Susan McCormick Ewoldt
*Assistant Examiner* — Karen Redden

(57) ABSTRACT

'KORfre0007' is a new and distinct variety of *Rosa hybrida* which is characterized by the combination of an upright growth habit, abundant recurrent stems and flowers which perform well as cut flowers, a very-double flower habit, a light pink flower color and also glossy, dark green foliage with above average disease resistance. The new variety propagates successfully by grafting and by stem cuttings and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORfre0007'.

BACKGROUND OF THE INVENTION

The present invention relates to a new and distinct *Rosa hybrida*, grandiflora rose cultivar, which has been given the variety denomination of 'KORfre0007'. Its market class is PLT/130.

Parentage: The *Rosa hybrida* variety 'KORfre0007' is the result of a controlled cross-pollination breeding program carried out by the inventor in Offenseth-Sparrieshoop, Germany. The objective of the said breeding program was to create a new and distinct rose plant with unique qualities, such as:

1. Uniform growth and flowering;
2. Abundant attractive, recurrent stems and flowers which perform well as cut flowers.
3. Attractive and abundant foliage; and
4. Resistance to diseases encountered in nursery and greenhouse culture.

This combination of qualities is not present in prior rose cultivars known to the inventor. These objectives have been substantially achieved and in that distinguish 'KORfre0007' from all other varieties known to the inventor.

'KORfre0007' is a seedling selection which resulted from the controlled pollination of two *Rosa hybrida* cultivars during the summer of 2001. Said cross-pollination was made between the seed parent, *Rosa hybrida* 'Meilavio' (U.S. Pat. No. 10,845), and the pollen parent, *Rosa hybrida* 'KORpastato' (unpatented).

As part of a rose development program, Tim-Hermann Kordes germinated seeds from the aforementioned hybridization during the winter of 2001 and conducted evaluations and observations on the resulting seedlings in a controlled environment in Offenseth-Sparrieshoop, Germany. The resulting seedlings exhibited distinctive physical and biological characteristics. The new rose plant was selected as a single plant in 2006 from the seedling beds due to its superior characteristics and asexually propagated for further evaluation. This new and distinctive rose variety was given the name 'KORfre0007'.

Asexual Reproduction: The first asexual propagation of 'KORfre0007' was done by budding to seedling understocks in 2007 at the inventor's nursery in Offenseth-Sparrieshoop, Germany. These initial and other subsequent propagations conducted in controlled environments demonstrate that 'KORfre0007' reproduces true to type in successive generations of asexual reproduction.

SUMMARY OF THE INVENTION

The following characteristics have been repeatedly observed and represent the distinguishing characteristics of the new *Rosa hybrida* cultivar 'KORfre0007'. These traits, in combination, distinguish 'KORfre0007' as a new and distinct cultivar.

1. *Rosa hybrida* 'KORfre0007' exhibits an upright habit; and

2. *Rosa hybrida* 'KORfre0007' exhibits a very-double flower habit; and
3. *Rosa hybrida* 'KORfre0007' exhibits abundant attractive, recurrent stems and flowers which perform well as cut flowers; and
4. *Rosa hybrida* 'KORfre0007' exhibits a light pink flower color, at anthesis; and
5. *Rosa hybrida* 'KORfre0007' exhibits glossy, dark green foliage; and
6. *Rosa hybrida* 'KORfre0007' exhibits above average disease resistance.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORfre0007', taken from plants of two years of age.

DETAILED BOTANICAL DESCRIPTION

The following is a detailed botanical description of a new and distinct variety of *Rosa hybrida* known as 'KORfre0007', based upon observations of plants of two years of age grown in nursery containers under conventional greenhouse production culture in May of 2015 at a nursery in Jackson County, Oreg.

Those skilled in the art will appreciate that certain characteristics will vary with older or, conversely, with younger plants. 'KORfre0007' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2001 edition except where common terms of color are used.

A botanical description of 'KORfre0007' and comparisons with other varieties of *Rosa hybrida* are provided below.

General plant description:

*Growth rate.*—Moderately vigorous to vigorous.

*Growth habit.*—Upright.

*Mature dimensions.*—Approximately 120 to 150 cm tall and 75 to 90 cm wide.

*Cold hardiness.*—To date, the variety has been grown successfully in USDA Hardiness Zone 7.

*Propagation.*—Grafting and stem cuttings.

*Disease resistance.*—Above average resistance to powdery mildew (*Sphaerotheca pannosa*) and blackspot (*Diplocarpon rosae*) diseases under normal growing conditions in Jackson County, Oreg.

Root system: Fibrous.

Stems:

*Stem color.*—Immature stems are Yellow-Green Group 144B; mature stems are Yellow-Green Group 144C.

*Intonations.*—Observed intonations of the immature stems are Greyed-Purple Group 184A; observed intonations of mature stems are Greyed-Red Group 182B.

*Stem surface texture.*—The surfaces of both immature and mature stems are smooth.

*Stem diameter.*—9 mm.

*Prickles.*—Incidence — Present; 20 prickles per 10 cm of stem, on average. Size — Length ranges from 3 to 9 mm. Immature prickle color — Greyed-Purple Group 184A. Mature prickle color — Greyed-Red Group 182B. Shape — Deeply concave. Texture — Smooth.

Leaves:

*Arrangement.*—Imparipinnate compound leaves; mature axillary leaves consisting of 5 leaflets.

*Attachment.*—Petiolate.

*Dimensions.*—150 mm long and 110 to 125 mm wide.

*Abundance.*—Very abundant.

*Stipules.*—Size — 15 to 25 mm long and 5 to 7 mm wide. Stipule color — Yellow-Green Group 144B. Anthocyanin — Greyed-Red Group 182B; present along the midrib. Stipitate glands — Abundant; only present along margins. Margins — Glandular toothed. Texture, adaxial surface — Glabrous. Texture, adaxial surface — Glabrous. Apex — Apiculate. Base — Winged.

*Petiole.*—Length — Average 30 to 40 mm. Diameter — Average 2 mm. Color, adaxial surface — Yellow-Green Group 144B. Color, abaxial surface — Yellow-Green Group 144B. Anthocyanin — Greyed-Purple Group 183C. Margins — Glandular toothed. Prickles — Several small prickle present on the abaxial surface. Stipitate glands — Limited number present on abaxial surface; abundant along margins. Texture, adaxial and abaxial surface — Papillate. Strength — Somewhat strong.

*Rachis.*—Length — Average 15 to 20 mm. Diameter — Average 1.5 mm. Color — Yellow-Green Group 144B. Anthocyanin — Greyed-Purple Group 183C. Margins — Glandular toothed. Texture — Papillate. Prickles — A few small prickles on the abaxial surface. Stipitate glands — Limited numbers of stipitate glands along margins and abaxial surface.

*Leaflets.*—Quantity — Mature axillary leaves normally consisting of 5 leaflets. Dimensions — Average size of the terminal leaflet is 65 to 80 mm long and 50 to 55 mm wide. Shape — Ovate. Apex — Acuminate. Base — Obtuse. Margins — Serrated. Texture, adaxial surface — Glossy and leathery. Texture, abaxial surface — Matte and leathery. Juvenile foliage color, adaxial surface — Yellow-Green Group 146A. Juvenile foliage color, abaxial surface — Yellow-Green Group 146B. Mature foliage color, abaxial surface — Yellow-Green Group 147A. Mature foliage color, abaxial surface — Yellow-Green Group 148B. Anthocyanin intonation — Greyed-Purple Group 184A. Present on juvenile foliage. Venation — Reticulate. Petiolule — Dimensions — 3 to 4 mm long and 2 mm in diameter. Petiolule color, adaxial surface — Yellow-Green Group 144C. Petiolule color, abaxial surface — Yellow-Green Group 144C. Prickles — None observed. Texture, adaxial surface — Smooth. Texture, adaxial surface — Papillate. Margins — Stipitate glands present along adaxial margins and on the abaxial surface.

Inflorescence:

*Inflorescence type.*—Both corymbs with multiple flowers and solitary flowers observed.

*Blooming habit.*—Recurrent.

*Quantity of flowers.*—Generally 1 to 4, on corymbs.

*Size.*—Corymbs are 110 to 140 mm tall and 120 to 150 mm wide, on average.

*Peduncle.*—Length — 60 to 80 mm, average length. Diameter — 5 to 7 mm, average diameter. Color — Yellow-Green Group 144A. Anthocyanin — Intonations of Greyed-Red Group 182A. Texture — Glabrous with prickles present. Strength — Strong.

Flowering laterals: Absent.

Bud:

*Bud form.*—Short and globular.

*Size.*—Upon opening, 50 mm in length from base of receptacle to distal end of bud and 50 mm diameter at its widest point.

*Texture.*—Leathery.

*Color, as sepals first unfold.*—White Group 155C with intonations of Red-Purple Group N57C.

*Color when one-quarter open, upper surface.*—Yellow Group 2D with intonations of Red-Purple Group N57D along margins.

*Color when one-quarter open, lower surface.*—White Group 155A with intonations of Red-Purple Group N57C along the margins. Outermost petals with intonations of Yellow-Green Group 144A.

Flower:

*Pedicel.*—Surface — Glabrous to lightly pubescent with abundant stipitate glands present. Length — 45 to 80 mm, on average. Diameter — 3 to 6 mm, on average. Color — Yellow-Green Group 144A, with intonations of Greyed-Red Group 184B. Strength — Strong. Texture — Papillate.

*Sepals.*—Diameter of Calyx — 65 to 75 mm at anthesis. Color, adaxial surface — Yellow-Green Group 147C. Color, abaxial surface — Yellow-Green Group 144A. Intonations — Greyed-Purple Group 185B. Size — 30 mm long and 10 mm wide, on average. Shape — Weak foliaceous appendages on 3 of the 5 sepals. Apex — Apiculate. Base — Flat at union with receptacle. Quantity — Five. Texture, adaxial surface — Hoary. Texture, abaxial surface — Smooth with limited number of fine white hairs present. Margins — Cilliate. Stipitate glands — Limited numbers present along margins.

*Corolla.*—Corolla habit — Very-double. General shape of corolla — Quartered rosette; round. Shape of corolla when viewed from the side — Upon opening, upper portion — Flat. Upon opening, lower portion — Concave. Open flower, upper portion — Flat. Open flower, lower portion — Concave. Aspect — Flowers held upright. Dimensions — Large for a floribunda rose. When open, the average corolla diameter is 95 to 100 mm and the average corolla height is 50 to 60 mm, from the top of the bloom to the base of the receptacle. Fragrance — Moderate. Duration — On the plant, 14 days. As a cut flower, 10 days. Senesced petals clinging. Petals — Petal Arrangement — Not formal. Petal Count — Approximately 75 petals under normal conditions. Petal Reflex — None observed. Petal Margin — Undulated. Petal Shape — Innermost petals are obovate; outermost petals are orbicular. Apex — Typically obtuse, with some retuse apices observed. Base — Innermost petals are attenuate; outermost petals are obtuse. Dimensions — Approximately 30 to 50 mm long and 30 to 55 mm wide. Texture, inner surface — Smooth. Texture, outer surface — Smooth. Petal color, upon opening — Outermost petals, outer surface — Marginal zone — Red-Purple Group N57D. Middle zone — Yellow Group 2D, with intonations of Red-Purple Group N57D. Basal zone — Yellow Group 2D. Outermost petals, inner surface — Marginal zone — Red-Purple Group N57D. Middle zone — Yellow Group 2D, with intonations of Red-Purple Group N57D. Basal zone — Yellow Group 2D. Innermost petals, outer surface — Marginal zone — Red Group 52C. Middle zone — Yellow Group 2D, with intonations of Red Group 52C. Basal zone — Yellow Group 2D. Innermost petals, inner surface — Marginal zone — Red Group 52D. Middle zone — Yellow Group 2D, with intonations of Red Group 52D. Basal zone — Yellow Group 2D. Basal petal spots, upon opening — Basal petal spot, outermost petals — Dimensions — 3 mm high and 5 mm wide. Color, outer surface — Not observed. Color, inner surface — Yellow Group 2B. Basal petal spot, innermost petals — Dimensions — 3 mm high and 3 mm wide. Outer surface — Yellow Group 2B. Inner surface — Yellow Group 2B. Petal color, after opening — Outermost petals, outer surface — White Group 155A, with intonations of Red-Purple Group N57C at and near the petal margins. Outermost petals, inner surface — Marginal zone — Red-Purple Group N57D. Middle zone — White Group 155B. Basal zone — Yellow Group 2D. Innermost petals, outer surface — Marginal zone — Red-Purple Group 62B. Middle zone — Red-Purple Group 62D. Basal zone — Yellow Group 2D. Innermost petals, inner surface — Marginal zone — Red-Purple Group N57D. Middle zone — Yellow Group 2D, with intonations of Red-Purple Group N57D. Basal zone — Yellow Group 2D. Basal petal spots, after opening — No distinct coloration at the petal base, at anthesis, is observed. General Tonality — Red-Purple Group 62A, at anthesis. No change in the general tonality at the end of the 10th day. Afterwards, general tonality is Red-Purple Group 62C. Petaloids— Quantity — 15 petaloids per flower, on average. Dimensions — Approximately 15 to 30 mm long and 10 to 30 mm wide. Color, inner surface — Marginal zone — Red-Purple Group N57C. Middle zone — Yellow Group 2D, with intonations of Red-Purple Group N57C. Basal zone — Yellow Group 2D. Color, outer surface — Marginal zone — Red-Purple Group N57C. Middle zone — Yellow Group 2D, with intonations of Red-Purple Group N57C. Basal zone — Yellow Group 2D. Texture, inner surface — Smooth. Texture, outer surface — Smooth. Margins — Undulated. Shape — Generally obovate; with many petaloids highly irregular. Apex — Obtuse. Base — Attenuate.

Reproductive organs:

*Stamens.*—Quantity — Approximately 110, on average, and regularly arranged around the styles. Anthers — Dimensions — 3 mm long and 1 mm wide, on average. Color — Yellow Group 2D.

Pollen — Generally present; medium density. Pollen Color — Greyed-Orange Group 163A. Filaments — Color — Yellow Group 2B, with intonations of Yellow-Orange Group 19A. Length — 5 to 7 mm.

*Pistils.*—Quantity — Abundant; approximately 90 present. Stigmas — Dimensions — 1 mm long and 1 mm wide. Location — Slightly superior and occasionally equal in position to anthers. Color — Yellow Group 3B. Styles — Length — Approximately 5 mm long. Color — White Group 155A.

*Ovary.*—Dimensions — 2.0 to 3.0 mm long and 1.5 mm in diameter. Color — Green-White Group 157D.

*Receptacle.*—Shape — Urn-shaped. Dimensions — Approximately 15 mm high and 10 mm wide. Surface — Glaucous. Color — Yellow-Green Group 144A, with intonations of Greyed-Purple Group 184B. Texture — Glabrous.

Hips and seed formation: Not observed.

COMPARISONS WITH THE PARENTS

The new rose plant may be distinguished from its seed parent, *Rosa hybrida* 'Meilavio', by the following combination of characteristics:

1. 'KORfre0007' exhibits a light pink general tonality of the corolla at anthesis, whereas 'Meilavio' exhibits a generally red corolla tonality, at anthesis.
2. 'KORfre0007' exhibits a peduncle length of 60 to 80 cm, whereas 'Meilavio' exhibits a peduncle length of 40 to 60 cm.

The new rose plant may be distinguished from its pollen parent, *Rosa hybrida* 'KORpastato', by the following combination of characteristics:

1. 'KORfre0007' exhibits a light pink general tonality of the corolla at anthesis, whereas 'KORpastato' exhibits a generally red tonality of the corolla at anthesis.
2. 'KORfre0007' exhibits an upright growth habit, whereas 'KORpastato' exhibits a spreading growth habit.

COMPARISONS WITH SIMILAR *ROSA HYBRIDA* CULTIVARS KNOWN TO THE INVENTOR

For a comparison, several physical characteristics of the *Rosa hybrida* variety 'KORtiglo' (U.S. Plant Pat. No. 19,385) are compared to 'KORfre0007' in Chart 1.

CHART 1

| Characteristic | 'KORfre0007' | 'KORtiglo' |
|---|---|---|
| General tonality of corolla, at anthesis. | Light pink, corresponding to Red-Purple Group 62A. | Yellow, corresponding to Yellow-Orange Group 20C. |
| Corolla dimensions. | 95 to 100 mm in diameter and 50 to 60 mm high. | 100 to 120 mm in diameter and 40 mm high. |
| Petal count. | Approximately 75. | Approximately 100 to 120. |
| Flower duration. | On the plant, 14 days. As a cut flower, 10 days. Senesced petals clinging. | On the plant, 4 to 6 days. As a cut flower, 5 to 6 days. Senesced petals drop away cleanly. |

That which is claimed:

1. A new and distinct variety of rose plant named 'KORfre0007', as described and illustrated herein.

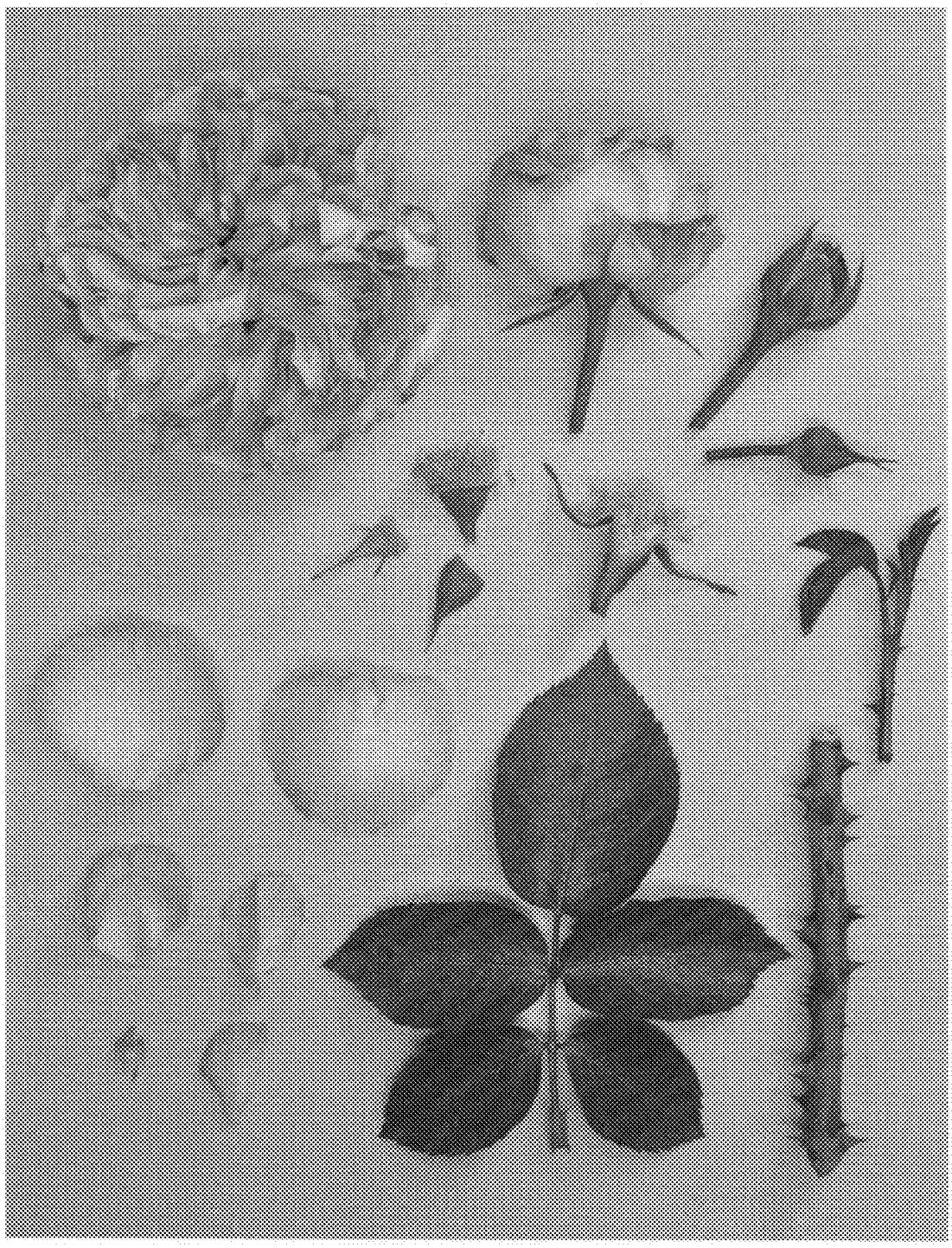

* * * * *